United States Patent
Isaacson

(10) Patent No.: US 8,678,999 B2
(45) Date of Patent: Mar. 25, 2014

(54) SYSTEM AND METHOD FOR A HYSTEROSCOPE WITH INTEGRATED INSTRUMENTS

(75) Inventor: Keith B. Isaacson, Newton, MA (US)

(73) Assignee: Karl Storz Endovision, Inc., Charlton, MA (US)

( * ) Notice: Subject to any disclaimer, the term of this patent is extended or adjusted under 35 U.S.C. 154(b) by 859 days.

(21) Appl. No.: 11/853,282

(22) Filed: Sep. 11, 2007

(65) Prior Publication Data

US 2008/0076966 A1 Mar. 27, 2008

Related U.S. Application Data

(60) Provisional application No. 60/825,217, filed on Sep. 11, 2006.

(51) Int. Cl.
*A61B 1/00* (2006.01)

(52) U.S. Cl.
USPC ........... 600/106; 600/104; 600/121; 600/123; 600/131

(58) Field of Classification Search
USPC ......... 600/131, 142, 156, 104–106, 129, 121, 600/123; 604/523–528
See application file for complete search history.

(56) References Cited

U.S. PATENT DOCUMENTS

| 4,258,721 A | 3/1981 | Parent et al. ................... 128/747 |
| 4,503,843 A | 3/1985 | Boebel .............................. 128/4 |
| 4,641,634 A | 2/1987 | Storz ................................ 128/4 |
| 4,779,611 A | 10/1988 | Grooters et al. ................... 128/4 |
| 4,836,189 A | 6/1989 | Allred, III et al. ................. 128/6 |
| 4,911,148 A | 3/1990 | Sosnowski et al. ................ 128/6 |
| 5,254,117 A * | 10/1993 | Rigby et al. ...................... 606/46 |
| 5,314,445 A | 5/1994 | Heidmueller née Degwitz et al. |
| 5,320,091 A | 6/1994 | Grossi et al. ....................... 128/4 |
| 5,441,503 A * | 8/1995 | Considine et al. .............. 606/46 |
| 5,716,321 A | 2/1998 | Kerin et al. ..................... 600/114 |
| 5,755,713 A * | 5/1998 | Bilof et al. ..................... 600/104 |
| 6,050,938 A | 4/2000 | Creed et al. .................... 600/101 |
| 6,059,719 A * | 5/2000 | Yamamoto et al. ........... 600/127 |
| 6,071,248 A * | 6/2000 | Zimmon ....................... 600/566 |
| 6,126,665 A * | 10/2000 | Yoon ............................. 606/144 |

(Continued)

FOREIGN PATENT DOCUMENTS

| EP | 1568305 A1 | 8/2005 |
| EP | 1568306 A1 | 8/2005 |

(Continued)

OTHER PUBLICATIONS

European Search Report; EP 07 81 1747; Sep. 30, 2009; 10 pages.

*Primary Examiner* — Matthew J Kasztejna
*Assistant Examiner* — Kevin G Barry, III
(74) *Attorney, Agent, or Firm* — St. Onge Steward Johnston & Reens LLC

(57) ABSTRACT

A hysteroscope includes a base and a handle attached to the base. The handle has a first trigger and a second trigger. An outer barrel is attached to the base. The outer barrel has a plurality of channels. An actuatable tool is located within at least one channel. The first trigger is in communication with the actuatable tool for extending the tool from within the at least one channel. The second trigger in communication with the actuatable tool for actuating the tool. The hysteroscope may further include a third trigger to pivot a distal portion of the outer barrel.

22 Claims, 10 Drawing Sheets

(56) References Cited

U.S. PATENT DOCUMENTS

| | | | |
|---|---|---|---|
| 6,196,966 B1 | 3/2001 | Kerin et al. | 600/114 |
| 6,210,330 B1 | 4/2001 | Tepper | 600/439 |
| 6,221,007 B1 | 4/2001 | Green | 600/160 |
| 6,261,307 B1* | 7/2001 | Yoon et al. | 600/101 |
| 6,328,734 B1 | 12/2001 | Zappala | 606/32 |
| 6,416,506 B1 | 7/2002 | Tilton, Jr. et al. | |
| 6,458,076 B1 | 10/2002 | Pruitt | 600/146 |
| 6,485,410 B1 | 11/2002 | Loy | 600/135 |
| 6,682,477 B2 | 1/2004 | Boebel et al. | 600/107 |
| 6,899,672 B2 | 5/2005 | Chin et al. | 600/121 |
| 8,231,524 B2* | 7/2012 | Schwartz et al. | 600/120 |
| 8,398,620 B2* | 3/2013 | Bacher et al. | 606/1 |
| 2001/0004676 A1* | 6/2001 | Ouchi | 600/106 |
| 2001/0018550 A1 | 8/2001 | Boebel et al. | 600/107 |
| 2002/0007110 A1* | 1/2002 | Irion | 600/170 |
| 2003/0004460 A1* | 1/2003 | Bedell | 604/95.04 |
| 2003/0125607 A1 | 7/2003 | Boebel et al. | 600/136 |
| 2003/0130563 A1 | 7/2003 | Loy | 600/114 |
| 2003/0130575 A1 | 7/2003 | Desai | 600/417 |
| 2003/0216717 A1 | 11/2003 | Nahen et al. | 606/3 |
| 2004/0193185 A1* | 9/2004 | McBrayer | 606/142 |
| 2004/0220478 A1 | 11/2004 | Wallace et al. | 600/476 |
| 2005/0021053 A1* | 1/2005 | Heinrich | 606/139 |
| 2005/0045183 A1 | 3/2005 | Callister et al. | 128/831 |
| 2005/0107665 A1 | 5/2005 | Nady | 600/116 |
| 2005/0125006 A1 | 6/2005 | Nady | 606/119 |
| 2005/0177145 A1 | 8/2005 | Nahen et al. | 606/15 |
| 2005/0197656 A1 | 9/2005 | Nahen et al. | 606/15 |
| 2005/0250989 A1* | 11/2005 | Suzuki | 600/106 |
| 2005/0255039 A1 | 11/2005 | Desai | 424/1.11 |
| 2005/0288551 A1* | 12/2005 | Callister et al. | 600/115 |
| 2006/0189845 A1* | 8/2006 | Maahs et al. | 600/146 |
| 2006/0258905 A1* | 11/2006 | Kaji et al. | 600/106 |
| 2006/0258955 A1* | 11/2006 | Hoffman et al. | 600/564 |
| 2009/0069632 A1* | 3/2009 | McIntyre et al. | 600/146 |

FOREIGN PATENT DOCUMENTS

| | | |
|---|---|---|
| GB | 2359492 A | 8/2001 |
| JP | 6054801 A | 3/1994 |
| JP | 2005211205 A | 8/2005 |

* cited by examiner

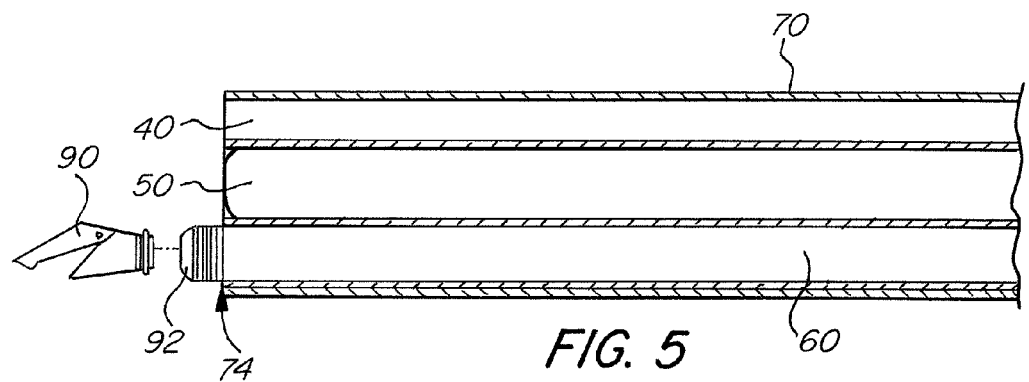
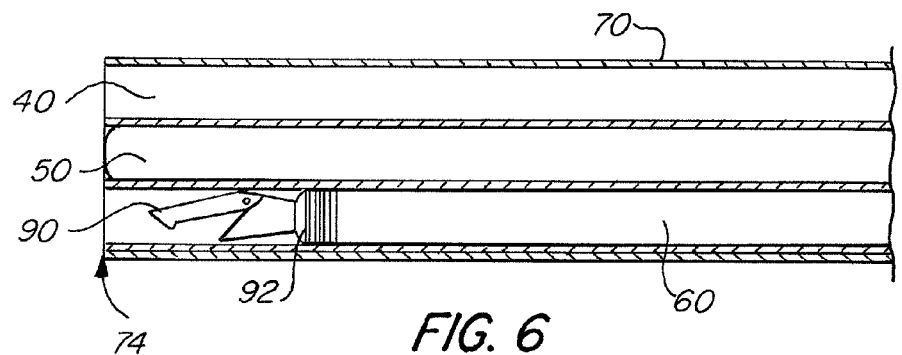

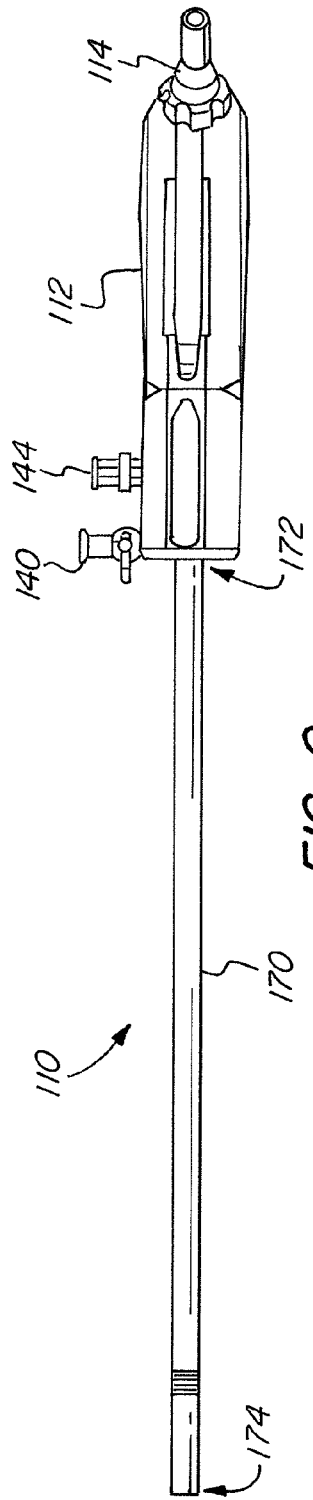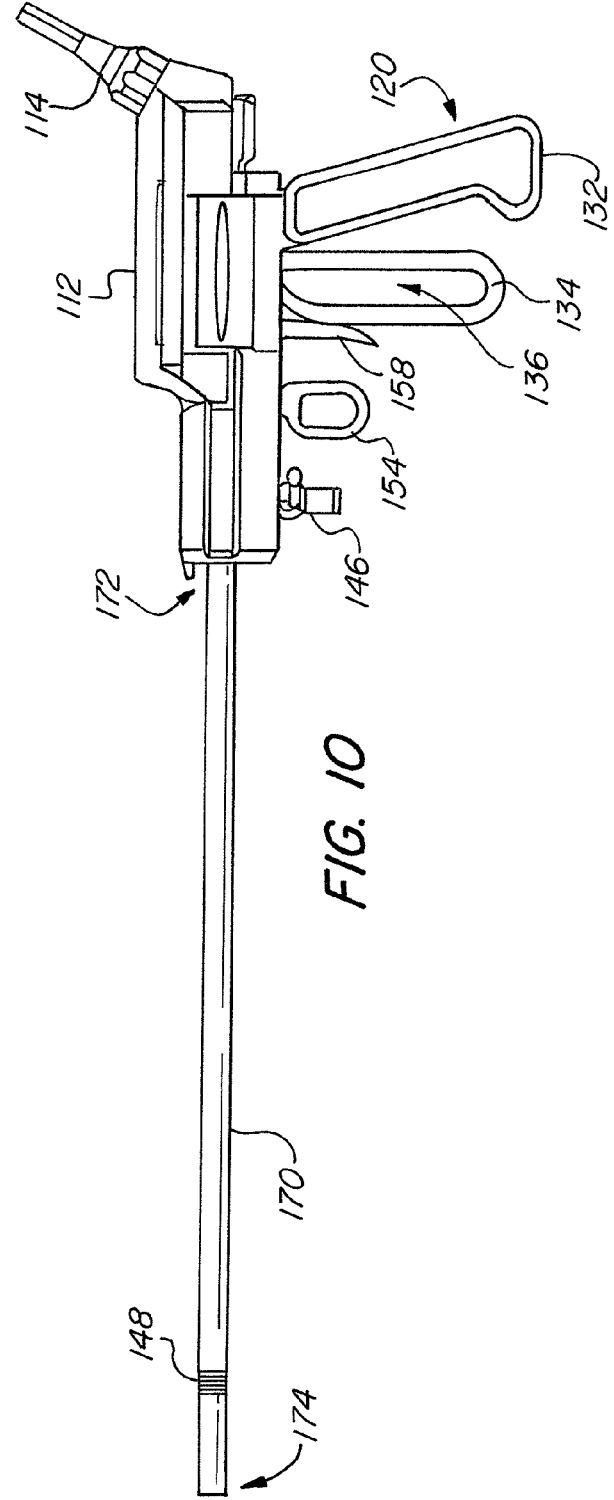

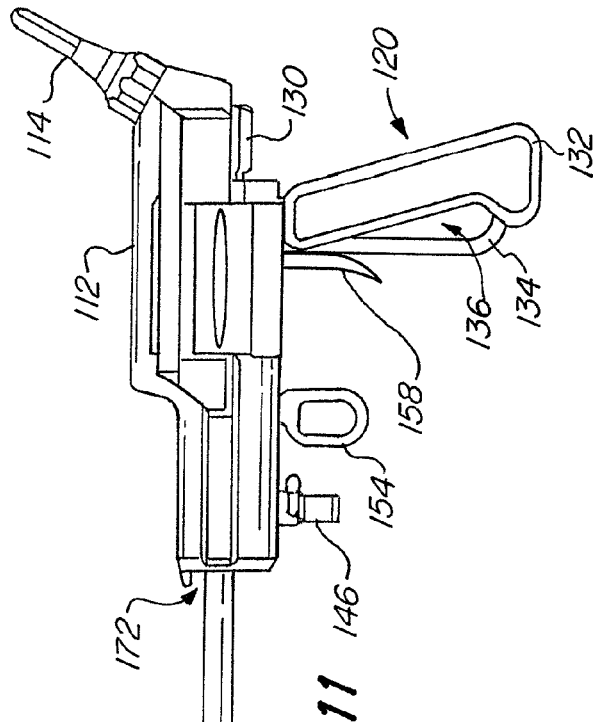
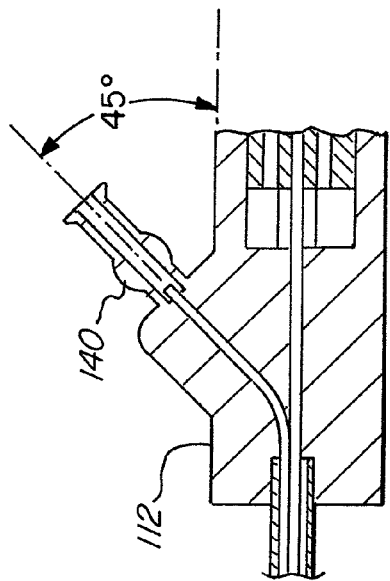
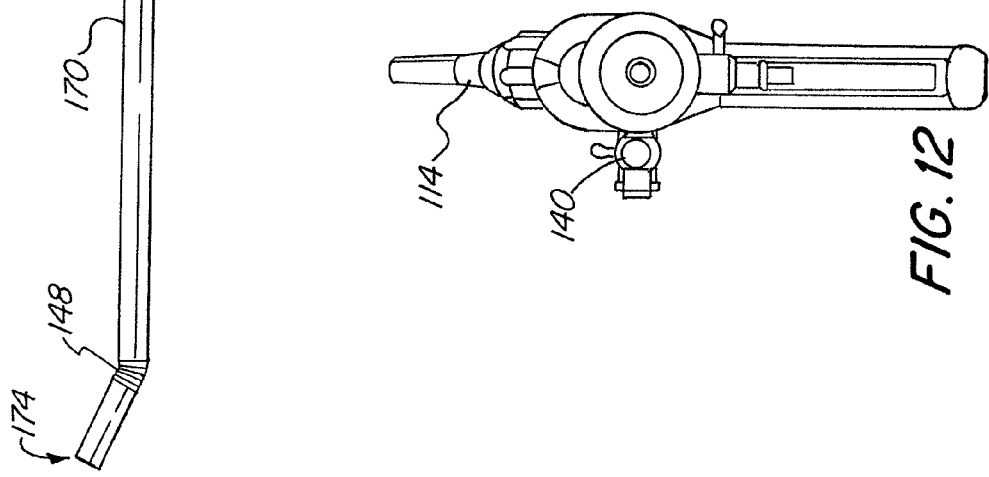
FIG. 11
FIG. 12
FIG. 13

SYSTEM AND METHOD FOR A HYSTEROSCOPE WITH INTEGRATED INSTRUMENTS

CROSS-REFERENCE TO RELATED APPLICATIONS

This application claims the benefit of, under 35 U.S.C. 119 (e), U.S. Provisional Patent Application No. 60/825,217, filed Sep. 11, 2006, which application is hereby incorporated by reference herein.

FIELD OF THE INVENTION

The present invention is generally related to an endoscope and, more particularly, a system and method for a hysteroscope conveniently operable by a single individual.

BACKGROUND OF THE INVENTION

Endoscopes and, particularly, hysteroscopes have added many features over the years. The features include in-flow and out-flow fluid transfer through one or more channels along a shaft of the hysteroscope, one or more optic channels along the shaft of the hysteroscope, wherein the optic equipment may be integral with the shaft or removable therefrom, electrical signal transfer along the shaft of the hysteroscope, insertion of various tools through one or more channels in the hysteroscope, including cutting, grasping, and guiding tools as well as catheters. With everything sliding in and out of the hysteroscope, often while the hysteroscope is in use, operation of the hysteroscope is at least a two-person job. Multiple people operating the hysteroscope can be difficult to coordinate and uncomfortable for the patient.

Thus, a heretofore unaddressed need exists in the industry to address the aforementioned deficiencies and inadequacies.

SUMMARY OF THE INVENTION

Embodiments of the present invention provide a system and method for individually operating a hysteroscope. Briefly described, in architecture, one embodiment of the system, among others, can be implemented as follows. The system contains a base and a handle attached to the base. The handle has a first trigger and a second trigger. An outer barrel is attached to the base. The outer barrel has a plurality of channels. An actuatable tool is located within at least one channel. The first trigger is in communication with the actuatable tool for extending the tool from within the at least one channel. The second trigger in communication with the actuatable tool for actuating the tool.

The present invention can also be viewed as providing methods for individually operating a hysteroscope. In this regard, one embodiment of such a method, among others, can be broadly summarized by the following steps: gripping a handle of a hysteroscope, wherein the handle is attached to a base, which is attached to an outer barrel; actuating a first trigger on the handle causing an actuatable tool within a channel of the outer barrel to extend from the channel; and actuating a second trigger causing the actuatable tool to actuate.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 5 is a cross-sectional view of a portion of the outer barrel of the hysteroscope of FIG. 1, in accordance with the exemplary embodiment of the present invention.

FIG. 6 is another cross-sectional view of a portion of the outer barrel of the hysteroscope of FIG. 1, in accordance with the exemplary embodiment of the present invention.

FIG. 9 is a top view of a hysteroscope, in accordance with another exemplary embodiment of the present invention.

FIG. 10 is a side view of the hysteroscope of FIG. 9, in accordance with the exemplary embodiment of the present invention.

FIG. 11 is another side view of the hysteroscope of FIG. 9, in accordance with the exemplary embodiment of the present invention.

FIG. 12 is a front view of the hysteroscope of FIG. 9, in accordance with the exemplary embodiment of the present invention.

FIG. 13 is a cross-sectional top view of a portion of the hysteroscope of FIG. 9, in accordance with the exemplary embodiment of the present invention.

DETAILED DESCRIPTION OF THE INVENTION

Figure 1:
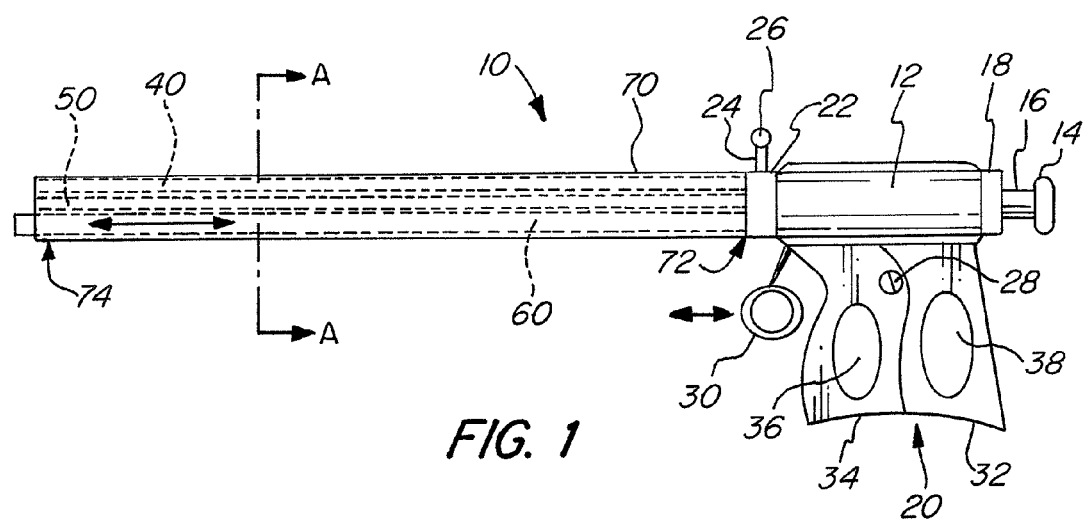
FIG. 1 is a side view of a hysteroscope, in accordance with one exemplary embodiment of the present invention.

FIG. 1 is a side view of a hysteroscope 10, in accordance with a first exemplary embodiment of the present invention.

The hysteroscope 10 includes a base portion 12. A handle 20 is integral with the base portion 12. The handle 20 includes a front handle portion 34 and a back handle portion 32, which are cooperatively operable as will be discussed further herein. A front handle opening 36 may be formed in the front handle portion 34 and a back handle opening 38 may be formed in the back handle portion 32 for the ease of operating the handle portions 32, 34. A locking element 28 is provided that may be used to lock the handle portions 32, 34 in a closed position, as shown in FIG. 1.

A trigger 30 may be provided at a front of the handle 20. The trigger 30 may be pivotable or slideable along the handle 20 and/or the base 12 in the directions indicated in FIG. 1. As is discussed in more detail below, the trigger 30 provides a means to extend a channel or tube of the hysteroscope 10, and/or a tool attached to or extending through the tube.

An outer barrel 70 is connected to the base portion 12 at a front seal 22. An external light source can be connected to a lens or fiberoptics within the scope with a post and connection depicted in 24 and 26. The outer barrel 70 encompasses a plurality of channels and is shown in cross-sectional form in FIG. 1. The plurality of channels includes an inflow tube 40, through which fluids may pass from a proximate end 72 of the outer barrel 70 to a distal end 74 of the outer barrel 70. The plurality of channels includes an outflow tube 60, through which fluids may pass from a distal end 74 of the outer barrel 70 to a proximate end 72 of the outer barrel 70. The plurality of channels includes an imagine system 50, which may be integral with the outer barrel 70 or may be removable. The imaging system 50 is in optic communication with a viewing opening 14 attached to the base 12 by a neck 16 at a rear seal 18.

The viewing opening 14 may simply consist of an ocular, not unlike a normal imaging system, that allows viewing through the distal end 74 of the outer barrel 70. The viewing opening 14 may also include a liquid crystal display ("LCD") screen, a lens (e.g., glass lens), a charge coupled device ("CCD") camera chip, a complementary metal oxide semiconductor ("CMOS") device, or a similar viewing apparatus that presents an image of the view through the distal end 74 of the outer barrel 70. Those having ordinary skill in the art will recognize other means of providing a view of an image at the distal end 74 of the outer barrel 70 to the viewing opening 14 and such means will be considered to be within the scope of the present invention.

Figure 2:
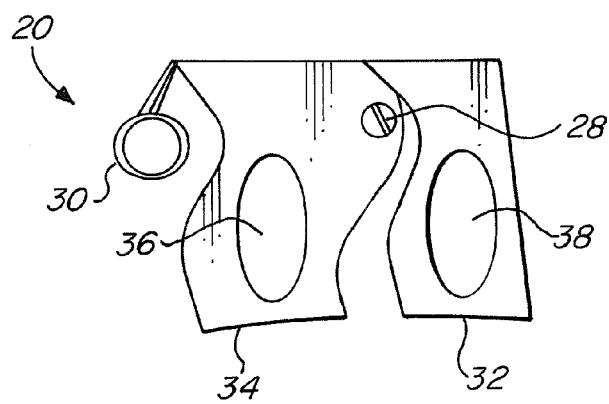
FIG. 2 is a side view of the handle for the hysteroscope of FIG. 1, in accordance with the exemplary embodiment of the present invention.

FIG. 2 is a side view of the handle 20 of the hysteroscope 10 shown in FIG. 1, in accordance with the first exemplary embodiment of the present invention. The handle 20 is shown in an open position in FIG. 2, as opposed to the closed position of the handle 20 in FIG. 1. In the open position, the front handle portion 34 and the back handle portion 32 are separated by a greater distance than the portions 32, 34 are in the closed position. The handle 20 may be used to actuate a tool, such as forceps (not shown). The forceps may traverse the length of the outer barrel 70, within, for instance, the outflow tube 60, and be operable beyond the distal end 74 of the outer barrel. Transferring the handle 20 between an open position and a closed position may operate to actuate the forceps from an open position to a closed position (e.g., scissor action). Other actuatable tools known in the art may be mechanically connected to the handle 20 and traverse the outer barrel 70 for actuation at or beyond the distal end 74 of the outer barrel 70 when the handle 20 is transferred between an open position and a closed position.

As forceps, for instance, may be a safety risk if left in an open position, the handle 20 and, therethrough, the forceps, may be locked in the closed position by the locking element 28. Similarly, the front handle portion 34 and the back handle portion 32 may be biased in a closed position by a spring or similar mechanical device to maintain a default closed position of the forceps or similar tool when the hysteroscope 10 is not in use. The trigger 30 will extend the tool beyond the tip of the hysteroscope when using the tool. The trigger 30 can then retract the tool within the hysteroscope channel 60 when the tool is not being used.

The trigger 30 may be operable to extend a tool, such as forceps, out of the distal end 74 of the outer barrel 70 or retract the tool within the outer barrel 70. Any tool protruding from the distal end 74 of the outer barrel 70 while the hysteroscope 10 is being inserted into a body cavity may create a trauma risk. By allowing the tool to be retracted within the outer barrel 70, the hysteroscope 10 may be inserted within a body cavity with minimized safety risks. Those having ordinary skill in the art will recognize many mechanical means for allowing such a tool to interact with the trigger 30 in a manner that permits retraction within the outer barrel 70 and extension beyond the distal end 74 of the outer barrel 70.

Figure 3:
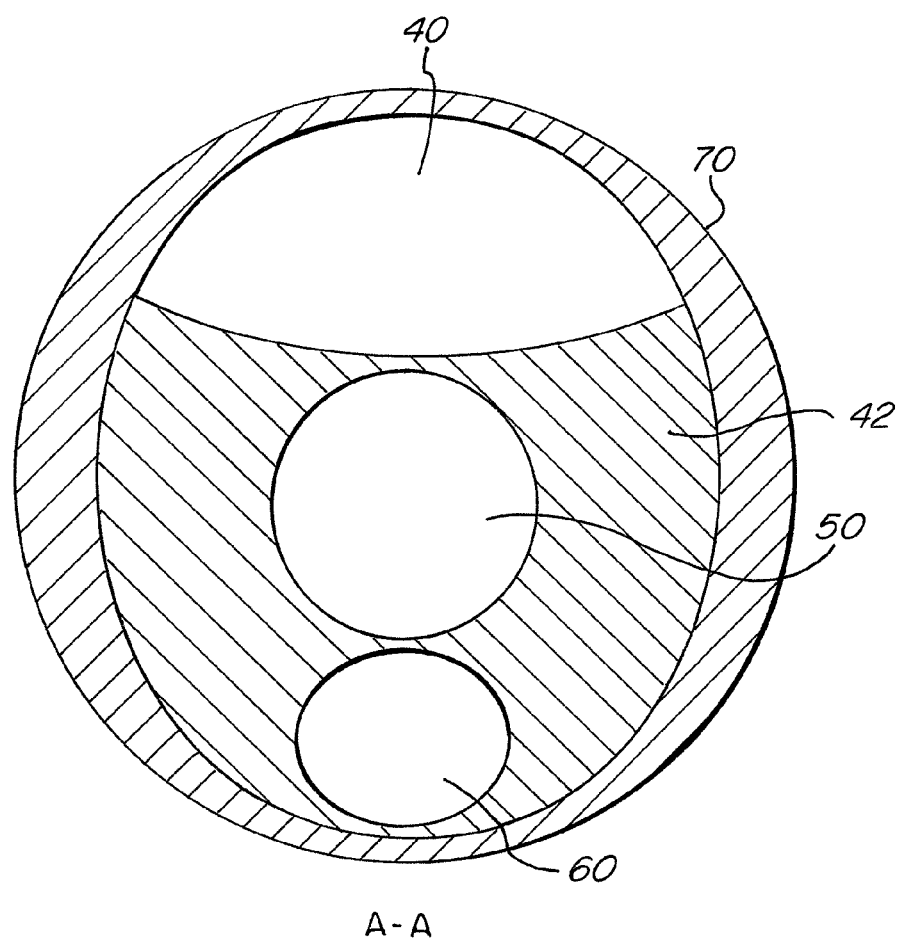
FIG. 3 is a cross-sectional front view of the outer barrel of the hysteroscope of FIG. 1, in accordance with the exemplary embodiment of the present invention.

FIG. 3 is a cross-sectional front view of the outer barrel 70 of the hysteroscope 10 of FIG. 1, in accordance with the first exemplary embodiment of the present invention. The outer barrel 70 encompasses the plurality of channels. The plurality of channels includes the inflow tube 40, through which fluids may pass from a proximate end 72 of the outer barrel 70 to a distal end 74 of the outer barrel 70. The plurality of channels includes the outflow tube 60 (e.g., working tube), through which fluids may pass from a distal end 74 of the outer barrel 70 to a proximate end 72 of the outer barrel 70. The plurality of channels includes the imaging system 50, which may be integral with the outer barrel 70 or may be removable.

As can be seen, the channels 40, 50, 60 need not be identically shaped or cylindrical. The space depicted in 42 can be filled with material to ensure the space around the described channels 60, 50, 40 will not need cleaning between uses. In the exemplary embodiment, the outer barrel 70 has an approximate diameter of 5.9 mm and the inflow tube 40 has an approximate height of 1.5 mm. The imaging system 50 and outflow tube 60 have approximate diameters of 2.5 mm and 2 mm, respectively. It should be understood however that these dimensions are only exemplary and that the present invention may be manufactured in any number of sizes to accommodate various applications.

Figure 4:
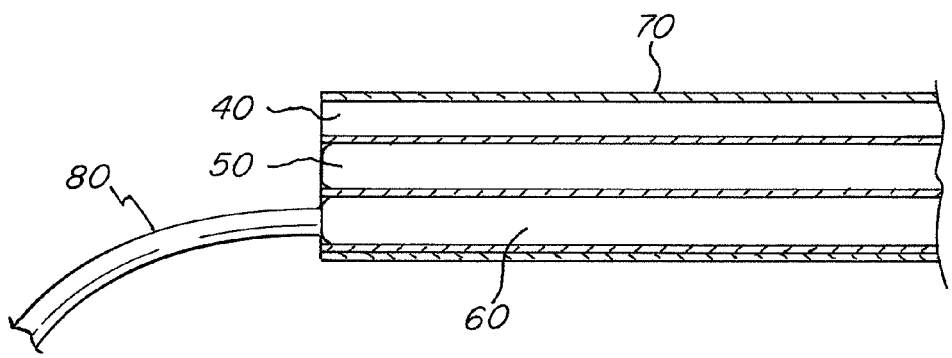
FIG. 4 is a side view of the distal end of the hysteroscope of FIG. 1 including an extended catheter guide that may be comprised of Nitinol.

FIG. 4 depicts the distal end of the hysteroscope including an extended malleable guide 80 for guiding tools or instruments, such as catheters, attached to the hysteroscope 10. For example, the guide 80 may attach to a distal end of the tube 60 or, in some embodiments, extend through a channel. The extended guide 80 may be comprised of a shape memory material such as Nitinol. Some guides 80 may be designed to curve in a particular direction (e.g., left, right) when extended. The guide 80 curves more the further it is extended. The extended guide 80 may be extended and/or retracted (e.g., within the outer barrel and/or tube 60) via the trigger 30. The extended guide 80 may further be retracted completely within the outer barrel 70.

FIG. 5 is a cross-sectional view of a distal end portion of the outer barrel 70 of the hysteroscope 10 of FIG. 1, in accordance with the first exemplary embodiment of the present invention. The outer barrel 70 encompasses the plurality of channels. The plurality of channels includes the inflow tube 40, the outflow tube 60, and the imaging system 50, which may be integral with the outer barrel 70 or may be removable. As shown in FIG. 5, the outflow tube 60 may be extended beyond the distal end 74 of the outer barrel 70.

The outflow tube 60 may further include a hollow screw 92 attachable to a disposable working head 90. The disposable working head 90 may, for instance, be used for a single patient and then discarded and replaced with another disposable working head for sanitary reasons. The disposable working head 90 and the hollow screw 92 may each include a helical rib allowing the disposable working head 90 and hollow screw 92 to mechanically engage and be disengaged. Those skilled in the art will recognize other means exist for making the disposable working head 90 and hollow screw 92 removably mechanical engageable, and those means are considered to be within the scope of the present invention.

FIG. 6 is another cross-sectional view of a distal end portion of the outer barrel 70 of the hysteroscope 10 of FIG. 1, in accordance with the first exemplary embodiment of the present invention. The outer barrel 70 encompasses the plurality of channels. The plurality of channels includes the inflow tube 40, the outflow tube 60, and the imaging system 50, which may be integral with the outer barrel 70 or may be removable. As shown in FIG. 6, the outflow tube 60 may be retracted within the distal end 74 of the outer barrel 70. The outflow tube 60 may further have a hollow screw 92 attachable to a disposable working head 90. The trigger 30 may control extension and retraction of the outflow tube 60. Biasing of either or both the trigger 30 and the outflow tube 60 may be used to maintain the outflow tube 60 in a primarily retracted position.

Figure 7:
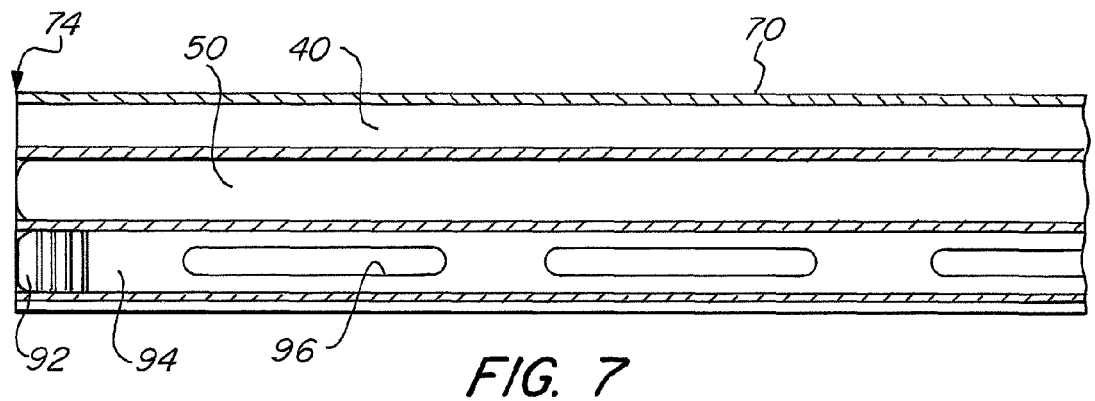
FIG. 7 is another cross-sectional view of a portion of the outer barrel of the hysteroscope of FIG. 1, in accordance with the exemplary embodiment of the present invention.

FIG. 7 is another cross-sectional view of a distal end portion of the outer barrel 70 of the hysteroscope 10 of FIG. 1, in accordance with the first exemplary embodiment of the present invention. The outer barrel 70 encompasses the plurality of channels. The plurality of channels includes the inflow tube 40 and the imaging system 50, which may be integral with the outer barrel 70 or may be removable. Also shown in FIG. 7 is a forceps tube 94. The forceps tube 94 may include the hollow screw 92. The forceps tube 94 may also include a plurality of slits 96. In some embodiments, the tube 94 extends through the outflow tube and is of smaller diameter than the outflow tube 60 allowing fluid to flow into the outflow tube 60 through slits 96. In some embodiments, the forceps tube 94 may be distinct from the outflow tube 60 in that the forceps tube 94 includes a shaft that is connected to the handle or a portion thereof (see, e.g., FIG. 18).

Figure 8:
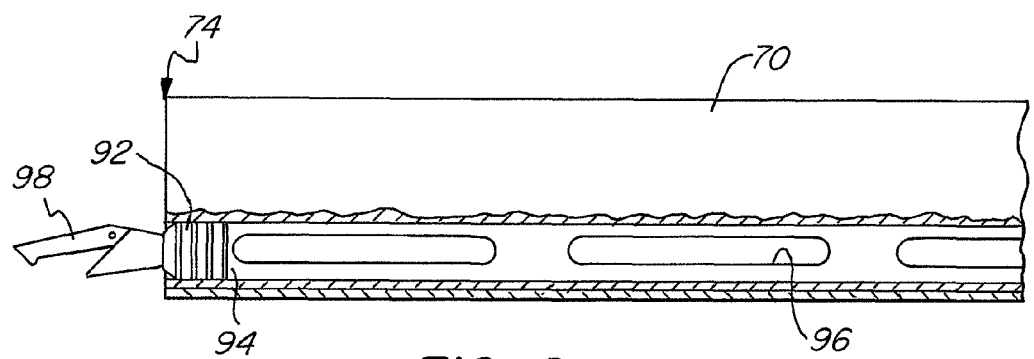
FIG. 8 is another cross-sectional front view of a portion of the outer barrel of the hysteroscope of FIG. 1, in accordance with the exemplary embodiment of the present invention.

FIG. 8 is another cross-sectional front view of a portion of the outer barrel 70 of the hysteroscope 10 of FIG. 1, in accordance with the first exemplary embodiment of the present invention. The outer barrel 70 encompasses the plurality of channels. The plurality of channels includes the inflow tube 40 and the imaging system 50, which may be integral with the outer barrel 70 or may be removable. As shown in FIG. 8, the outer barrel 70 further includes a forceps tube 94 in the exemplary embodiment.

The forceps tube 94 may also include a plurality of slits 96. The forceps tube 94 may further have a hollow screw 92 attachable to a disposable forceps head 98. The disposable forceps head 98 may, for instance, be used for a single patient and then discarded and replaced with another disposable working head for sanitary reasons. The disposable forceps head 98 and the hollow screw 92 may each include a helical rib allowing the disposable forceps head 98 and hollow screw 92 to mechanically engage and be disengaged. Those skilled in the art will recognize other means exist for making the disposable forceps head 98 and hollow screw 92 removably mechanical engageable, and those means are considered to be within the scope of the present invention. The trigger 30 may control extension and retraction of the forceps tube 94. Biasing of either or both the trigger 30 and the outflow tube 60 may be used to maintain the forceps tube 94 in a primarily retracted position.

FIG. 9 is a top view of a hysteroscope 110, in accordance with another exemplary embodiment of the present invention. The hysteroscope 110 includes a base portion 112. An outer barrel 170 is connected to the base portion 112. The outer barrel 170 includes a plurality of channels, a proximate end 172 and a distal end 174. A light post 144 is integral with the base 112. The light post 144 may be used to generate or feed light into at least one of the channels and out the distal end 174 of the outer barrel 170. The camera assembly is attached to a power source and data source such as a USB cord at the viewing opening or post 114. An egress portion of the fluid inflow channel is depicted on this top view as 140.

FIG. 10 is a side view of the hysteroscope 110 of FIG. 9. A handle 120 is integral with the base portion 112. The handle 120 includes a front handle portion 134 and a back handle portion 132, which are cooperatively operable as discussed herein. A front handle opening 136 may be formed in the front handle portion 134 for the ease of operating the front handle portion 134. In some embodiments, a tool is attached to the handle portion 134 and/or the handle portion 132. The handle portion 134 can then be removed from the handle 120, together with the tool, to replace the disposable tools. The tool can also be extended or retracted through the barrel 170 using the trigger 158.

The outer barrel 170 encompasses a plurality of channels. The plurality of channels includes an outflow tube 160, through which fluids may pass from a distal end 174 of the outer barrel 170 to a proximate end 172 of the outer barrel 170. An outflow port 146 is integral with the base 112 and in fluid communication with the outflow tube 160 (see, e.g., FIGS. 10 and 14). Outflow fluids may be released through the outflow port 146. Sealing or plugging the outflow port 146 may allow one to limit or regulate distention fluids from the body cavity.

Some exemplary embodiments further include a pivot trigger 154 provided at a front of the handle 120. The pivot trigger 154 may be pivotable or slideable along the handle 120 and/or the base 112. Actuation of the pivot trigger 154 may cause the distal end 174 of the outer barrel 170 to pivot or rotate along pivot joint 148. While the distal end 174 of the outer barrel 170 may be mobile along the pivot joint 148, the remainder of the outer barrel 170 is relatively inflexible from the proximate end 172 of the outer barrel 170 to the pivot joint 148. Means of actuation of a pivot joint 148 from a pivot trigger 154 is a mechanical activity that is known to those skilled in the art and all such means are considered to be within the scope of the present invention.

The plurality of channels includes an imaging system 150, which may be integral with the outer barrel 170 or may be removable. The imaging system 150 is in optic communication with the viewing opening 114 attached to the base 112. The viewing opening 114 may simply consist of an ocular, not unlike a normal imaging system, that allows viewing through the distal end 174 of the outer barrel 170. The viewing opening 114 may consist of an LCD screen or similar viewing apparatus that presents an image of the view through the distal end 174 of the outer barrel 170. The viewing opening 114 may be rotatable such that rotating the viewing opening 114 rotates orientation of an image viewed. Those having ordinary skill in the art will recognize other means of providing a view of an image at the distal end 174 of the outer barrel 170 to the viewing opening 114 and such means will be considered to be within the scope of the present invention.

FIG. 11 is another side view of the hysteroscope 110 of FIG. 9. The handle 120 is integral with the base portion 112. The handle 120 includes the front handle portion 134 and the back handle portion 132, which are cooperatively operable and may mesh together, as shown in FIG. 11. A locking element may be provided that may be used to lock the handle portions 132, 134 in a closed position (the position shown in FIG. 11 relative to FIG. 10 is a closed position).

Figure 18:
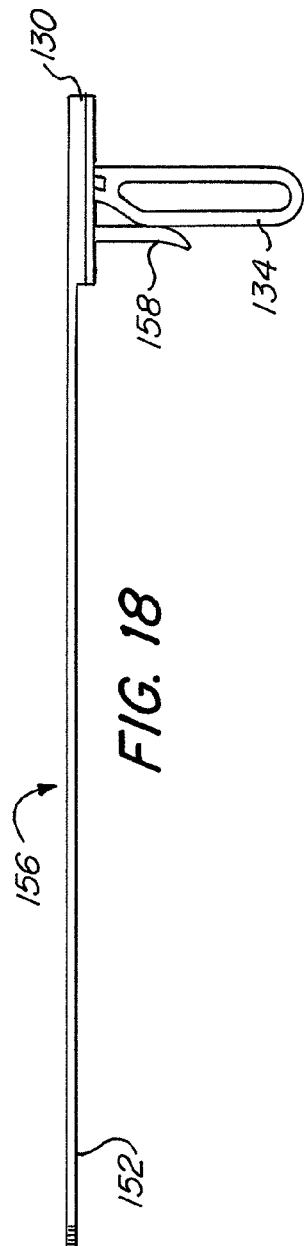
FIG. 18 is a side view of a portion of the hysteroscope of FIG. 9.

A tool or tool assembly 156, such as forceps, may be provided within one of the channels of the outer barrel 170 (see, e.g., FIG. 18). A tool retract trigger 158 is provided as part of the tool assembly 156. The tool retract trigger 158 is in communication with the forceps 156. Actuation of the tool retract trigger 158 will draw the forceps 156 back to within the channel. A tool extend button 130 is also provided in communication with the forceps 156. Actuation of the tool extend button 130 will extend the forceps 156 from within the channel. As would be understood by one having ordinary skill in the art, the tool retract trigger 158 and the tool extend button 130 operate in a complimentary fashion.

As can be seen in FIG. 11, the distal end 174 of the outer barrel 170 is deflected at the pivot joint 148. The deflection is caused by actuation of the pivot trigger 154. While the distal end 174 of the outer barrel 170 may be mobile along the pivot joint 148, the remainder of the outer barrel 170 is relatively inflexible from the proximate end 172 of the outer barrel 170 to the pivot joint 148. Means of actuation of a pivot joint 148 from a pivot trigger 154 is a mechanical activity that is known to those skilled in the art and all such means are considered to be within the scope of the present invention.

FIG. 12 is a front view of the hysteroscope 110 of FIG. 9. FIG. 13 is inside view of a portion of the hysteroscope 112 of FIG. 9, in accordance with the second exemplary embodiment of the present invention. These figures illustrate an egress of the inflow tube 140. The egress is mateable with other devices for providing fluids, as is known to those having ordinary skill in the art.

Figure 14:
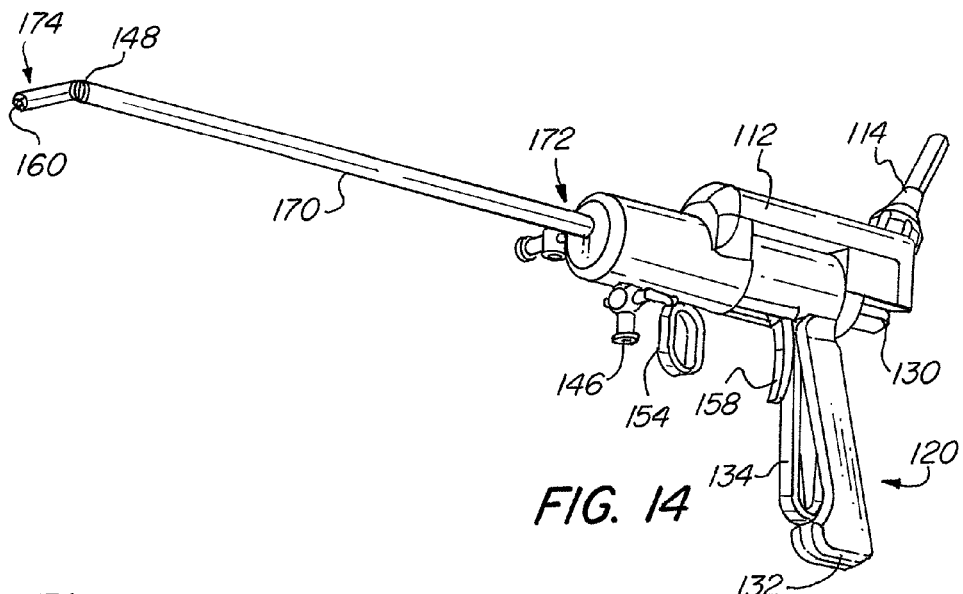
FIG. 14 is a perspective front view of the hysteroscope of FIG. 9, in accordance with the exemplary embodiment of the present invention.
Figure 15:
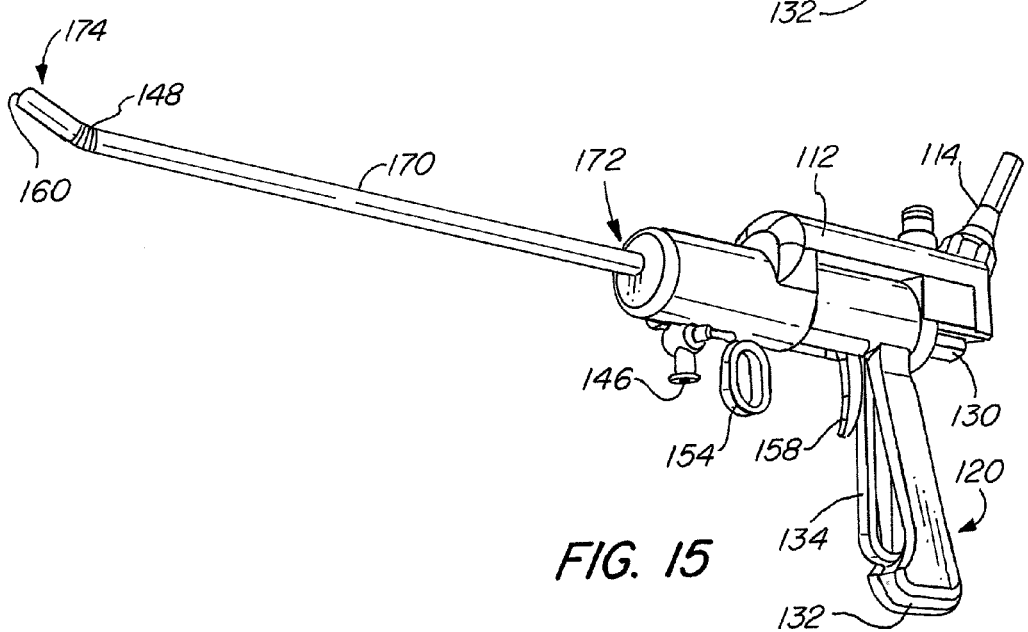
FIG. 15 is another perspective front view of the hysteroscope of FIG. 9, in accordance with the exemplary embodiment of the present invention.
Figure 16:
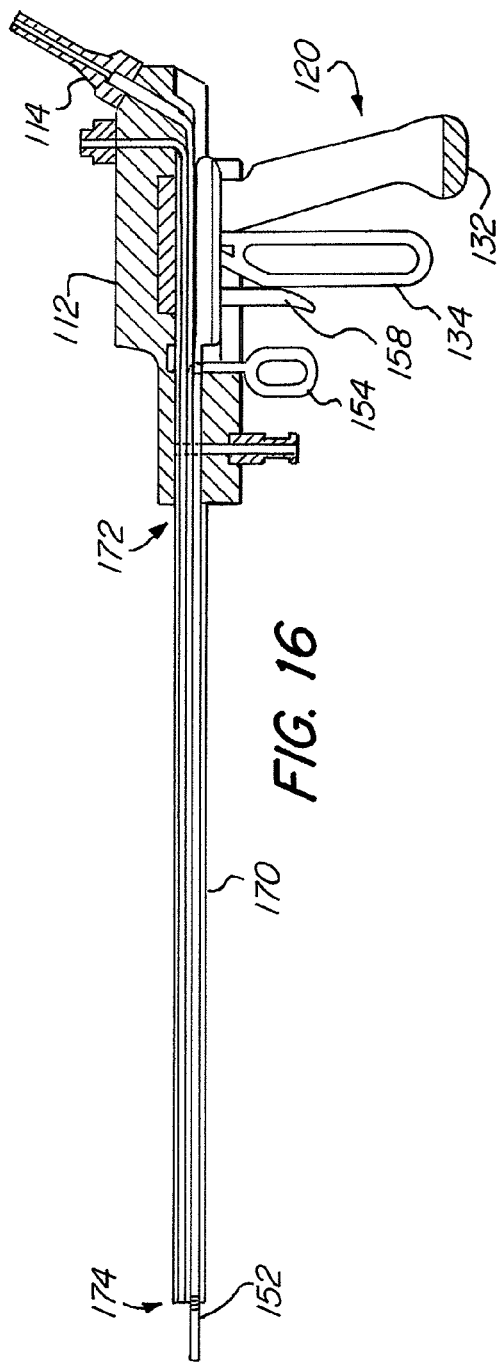
FIG. 16 is a cross-sectional side view of the hysteroscope of FIG. 9.
Figure 17:
FIG. 17 is a top view of a portion of the hysteroscope of FIG. 9.

FIG. 14 is a perspective front view of the hysteroscope 110 of FIG. 9, in accordance with the second exemplary embodiment of the present invention. FIG. 15 is another perspective front view of the hysteroscope 110 of FIG. 9, in accordance with the second exemplary embodiment of the present invention. These figures illustrate available deflection angles for the distal end 174 of the outer barrel 170 along the pivot joint 148. The trigger will change the angle of deflection through a steering wire mechanism.

Figure 19:
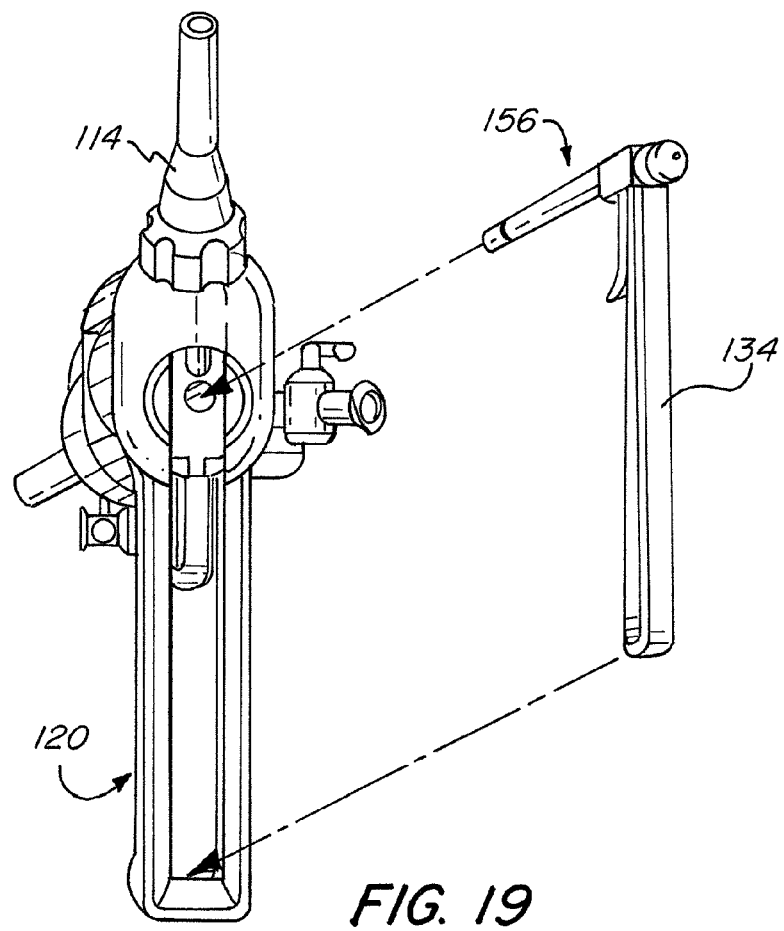
FIG. 19 is a front view of the hysteroscope of FIG. 9.

FIGS. 16-19 show an exemplary embodiment of the hysteroscope 110 including a tool assembly 156. The assembly 156 includes a tool shaft 152 insertable through the outer barrel 170 and/or one of the channels tubes (e.g., 160) of the outer barrel 170. The shaft 152 may include a tool (e.g., forceps) on its distal end. The assembly 156 further includes the handle portion 134 and the retraction trigger 158. The handle portion 132 is attached (e.g., removably) to the base 112 in the present embodiment. As shown in FIG. 19, the tool assembly 156 may be readily inserted and removed from the hysteroscope 110 for ease of tool replacement.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

What is claimed is:

1. A hysteroscope comprising:
a base having a longitudinal axis;
a handle attached to said base and extending substantially perpendicular to said base, said handle having a first trigger and a second trigger, wherein the second trigger has a front handle portion and a back handle portion;
an outer barrel having a plurality of channels extending from a proximate end of said outer barrel to a distal end of said outer barrel, where said outer barrel is attached to said base and where the longitudinal axis of the base and the longitudinal axis of the outer barrel are collinear;
a joint along said outer barrel;
a third trigger in communication with said joint for deflecting or rotating a distal portion of the outer barrel at said joint, said third trigger attached to said base and provided at a front of said handle in a location between the outer barrel and the first and second triggers, said third trigger being slidable along the base and displaceable from a first position to a second position along the longitudinal axis of the base, where the third trigger is able to be actuated in both the first position and the second position;
an actuatable tool located within at least one of the channels;
wherein the first trigger is in communication with the actuatable tool for extending the tool from within the at least one channel; and
wherein the second trigger is in communication with the actuatable tool for actuating a head of the tool;
wherein the first and second triggers are displaceable in a direction along a length of said outer barrel, said front handle portion and said back handle portion being cooperatively operable so that in a closed position said front handle portion is flush against said back handle portion.

2. The hysteroscope of claim 1 wherein the actuatable tool is a forceps.

3. The hysteroscope of claim 1, wherein the first trigger is further for retracting the tool within the at least one channel.

4. The hysteroscope of claim 1, wherein at least one of the channels includes a working tube extending through the channel from the proximate end of said outer barrel to the distal end of said outer barrel; wherein the actuatable tool is connectable to a distal end of the working tube; and wherein the first trigger extends the working tube and actuatable tool.

5. The hysteroscope of claim 4, wherein the working tube includes a hollow screw portion at the distal end of the working tube for receiving the actuatable tool.

6. The hysteroscope of claim 5, wherein the working tube includes two or more slits to allow fluid to flow through the channel via the slits.

7. The hysteroscope of claim 1, wherein actuation of the third trigger further changes a direction in which the distal portion of the outer barrel is extended.

8. The hysteroscope of claim 1, wherein the plurality of channels include an inflow channel for transferring fluid from the proximate end of the outer barrel to the distal end of the outer barrel, an outflow channel for transferring fluid from the distal end of the outer barrel to the proximate end of the outer barrel, and an imaging system channel.

9. The hysteroscope of claim 8, wherein said actuatable tool is located within the outflow channel.

10. The hysteroscope of claim 8, wherein the first trigger is further for extending the outflow channel relative to the outer barrel.

11. The hysteroscope of claim 1, further comprising:
at least one extendable guide in communication with a channel and extendable via a distal end of the outer barrel; and
wherein the extendable guide comprises a shape memory material.

12. The hysteroscope of claim 11, wherein the extendable guide curves in one particular direction following extension.

13. The hysteroscope of claim 11, wherein the shape memory material is Nitinol.

14. The hysteroscope of claim 1, further comprising:
a locking mechanism for locking at least one of the first trigger and second trigger.

15. The hysteroscope of claim 1, further comprising a spring.

16. The hysteroscope of claim 15, wherein said spring maintains a closed position of the hysteroscope when the hysteroscope is not in use.

17. The hysteroscope of claim 1, wherein said third trigger is not a knob.

18. The hysteroscope of claim 1, wherein said third first and second triggers are complimentary in shape to one another.

19. A method for individually operating a hysteroscope, comprising the steps of:
gripping a handle of a hysteroscope, wherein the handle is attached to a base and extends substantially perpendicular to the longitudinal axis of the base, which is attached to an outer barrel where the longitudinal axis of the base and the longitudinal axis of the outer barrel are collinear;
positioning the hysteroscope using the handle;
actuating a first trigger on the handle by displacing the first trigger in a direction along a length of said outer barrel causing an actuatable tool within a channel of the outer barrel to extend from a distal end of the channel;
actuating a second trigger by displacing the second trigger in a direction along a length of said outer barrel causing the actuatable tool to actuate, said second trigger being cooperatively operable with said first trigger, said second trigger having a front handle portion and a back handle portion; and
actuating a third trigger in communication with a joint along said outer barrel to deflect or rotate a distal portion of the outer barrel at the joint, said third trigger attached to said base between the outer barrel and the first and second triggers, said third trigger being slidable along the base and displaceable from a first position to a second position along the longitudinal axis of the base, where the third trigger is able to be actuated in both the first position and the second position,
wherein the first and second triggers are displaceable in a direction along a length of said outer barrel,
wherein said front handle portion and said back handle portion being cooperatively operable so that in a closed position said front handle portion is flush against said back handle portion.

20. The method of claim 19, wherein the tool is a forceps.

21. The method of claim 19, further comprising the step of:
actuating the first trigger to retract the actuatable tool.

22. The method of claim 19, further comprising the step of:
actuating the third trigger to change a direction in which the distal portion of the outer barrel is extended.

* * * * *